(12) United States Patent
Miura (10) Patent No.: US 7,010,963 B2
(45) Date of Patent: Mar. 14, 2006

(54) LIQUID DETECTING APPARATUS (75) Inventor: Shinsuke Miura, Shizuoka-ken (JP)

(73) Assignee: CBC Materials Co., Ltd., Tokyo (JP)

( * ) Notice: Subject to any disclaimer, the term of this patent is extended or adjusted under 35 U.S.C. 154(b) by 186 days.

(21) Appl. No.: 10/698,389

(22) Filed: Nov. 3, 2003

(65) Prior Publication Data

US 2004/0237633 A1    Dec. 2, 2004

(30) Foreign Application Priority Data

Nov. 20, 2002   (JP)  ............................. 2002-337064

(51) Int. Cl.
  *G01N 11/10*   (2006.01)
(52) U.S. Cl. .................. 73/54.24; 73/54.24; 73/54.41; 73/54.27; 73/54.25
(58) Field of Classification Search ............... 73/54.24, 73/54.41, 54.27, 54.25
See application file for complete search history.

(56) References Cited

U.S. PATENT DOCUMENTS

| | | | | |
|---|---|---|---|---|
| 4,240,285 A | * | 12/1980 | Langdon | ..................... 73/32 A |
| 4,857,792 A | * | 8/1989 | Miura et al. | ........... 310/323.02 |

FOREIGN PATENT DOCUMENTS

| | | |
|---|---|---|
| JP | 8-86733 | 4/1996 |
| JP | 8-247917 | 9/1996 |

\* cited by examiner

*Primary Examiner*—Hezron Williams
*Assistant Examiner*—André K. Jackson
(74) *Attorney, Agent, or Firm*—Wenderoth, Lind & Ponack, L.L.P.

(57) ABSTRACT

Piezoelectric plates conduct bending vibrations and are axially symmetrical about the vibration shaft so the piezoelectric plates conduct a bending vibration, lower vibrating ends of the piezoelectric plates are rigidly connected to a vibration suppressing member and upper vibration ends of the piezoelectric plates are rigidly connected to the vibration shaft, an inner edge of each of the piezoelectric plates excluding the vibration connection part is free of the vibration shaft, a bending vibration at the lower vibrating end of each of the piezoelectric plates is suppressed on the vibration suppression connection part side and a bending vibration at the upper vibrating end is amplified and then applied to the vibration shaft and the liquid detecting element which is disposed at a lower end of the vibration shaft, through the vibration connection part, so that the liquid detecting element is vibrated in the circular direction in the measuring liquid.

2 Claims, 8 Drawing Sheets

LIQUID DETECTING APPARATUS

BACKGROUND OF THE INVENTION

1. Field of the Invention

The present invention relates to a liquid detecting apparatus which constitutes a viscometer or density meter for detecting density of a measuring liquid, and more particularly to a liquid detecting apparatus in which a vibrating element composed of a piezoelectric vibrating plate is used as a vibrating source.

2. Related Art

Patent documents 1 and 2 disclose a liquid detecting apparatus comprising a liquid detecting element located at a lower end of a vibration shaft and immersed in a measuring liquid and a vibrating element located at an upper end of the vibration shaft and for vibrating the vibration shaft in a circular direction about the axis of the vibration shaft, wherein a piezoelectric vibrating plate capable of conducting a bending vibration is used as the vibration detecting element and the vibration shaft is vibrated in the circular direction by the bending vibration of the piezoelectric vibrating plate, thereby vibrating the liquid detecting element in the circular direction in the measuring liquid.

In the liquid detecting apparatus as represented by the above patent documents 1 and 2, the inner end edges of the respective piezoelectric vibrating plates are rigidly connected to the vibration shaft on their generating line, and a massive body is rigidly connected to the upper vibrating end on the opposite side of the liquid detecting element of each piezoelectric vibrating plate and the upper end of the vibration shaft, so that vibrations of the liquid detecting element are caused to occur in the circular direction in the measuring liquid by bending vibration of the lower vibrating end on the liquid detecting element side. Since each piezoelectric vibrating plate is rigidly connected at two sides along its upper vibrating end and inner end edge to the massive body and the vibration shaft, respectively, energy for transmitting vibration to the vibration shaft is reduced. As a result, energy for transmitting vibration to the liquid detecting element is reduced, thereby reducing the active vibration in the circular direction in the measuring liquid.

In addition, since the massive body, the vibrating plate and the vibration shaft are coaxially arranged in series, the overall length of the vibration unit becomes unduly large.

[Patent Document 1]
Official gazette of Japanese Patent Application Laid-Open No. H08-247917

[Patent Document 2]
Official gazette of Japanese Patent Application Laid-Open No. H08-86733

SUMMARY OF THE INVENTION

It is, therefore, a general object of the present invention to provide a liquid detecting apparatus capable of solving the above-mentioned problems.

In order to solve the above problems, there is provided a liquid detecting apparatus comprising a liquid detecting element disposed at a lower end of a vibration shaft and immersed in a measuring liquid, and a vibrating element disposed at an upper end of the vibration shaft and for vibrating the vibration shaft in a circular direction about an axis thereof, wherein a plurality of piezoelectric vibrating plates, which each conduct a bending vibration, are used as the vibrating element and axially symmetrically arranged in the axial direction with respect to the vibration shaft so that the piezoelectric vibrating plates conduct a bending vibration, lower vibrating ends on the liquid detecting element side of the piezoelectric vibrating plates are rigidly connected (vibration suppressing connection) to a vibration suppressing member and inner ends of upper vibration ends on the side opposite the liquid detecting element of the piezoelectric vibrating plates are rigidly connected (vibration connection) to the vibration shaft, an inner end edge of each of the piezoelectric vibrating plates excluding the vibration connection part is held free with respect to the vibration shaft, a bending vibration at the lower vibrating end of each of the piezoelectric vibrating plates is suppressed on the vibration suppression connection part side and a bending vibration at the upper vibrating end is amplified, the amplified bending vibration at each vibrating end is applied to the vibration shaft and the liquid detecting element through the vibration connection part, so that the liquid detecting element is vibrated in the circular direction in the measuring liquid.

From another aspect of the present invention, there is also provided a liquid detecting apparatus comprising a liquid detecting element disposed at a lower end of a vibration shaft and immersed in a measuring liquid, and a vibrating element disposed at an upper end of the vibration shaft and for vibrating the vibration shaft in a circular direction about an axis thereof, wherein a plurality of piezoelectric vibrating plates, which each conduct a bending vibration, are used as the vibrating element and axially symmetrically arranged in the axial direction with respect to the vibration shaft so that the piezoelectric vibrating plates conduct a bending vibration, a cylindrical member is provided and has, as an axis thereof, the vibration axis for connecting the inner end edges of the piezoelectric vibrating plates, each of the piezoelectric vibrating plates is externally inserted in an upper end of the vibration shaft at the cylindrical member, lower vibrating ends on the liquid detecting element side of the piezoelectric vibrating plates are rigidly connected (vibration suppressing connection) to a vibration suppressing member and inner ends of upper vibration ends on the side opposite the liquid detecting element of the piezoelectric vibrating plates are rigidly connected (vibration connection) to the vibration shaft, an inner end edge of each of the piezoelectric vibrating plates excluding the vibration connection part is held free with respect to the vibration shaft, a bending vibration at the lower vibrating end of each of the piezoelectric vibrating plates is suppressed on the vibration suppression connection part side and a bending vibration at the upper vibrating end is amplified, the amplified bending vibration at each vibrating end is applied to the vibration shaft and the liquid detecting element through the vibration connection part, so that the liquid detecting element is vibrated in the circular direction in the measuring liquid.

Preferably, a through-hole having the vibration axis serving as an axis thereof is formed in the vibration suppressing member, the vibration shaft is inserted in the through-hole and the piezoelectric vibrating plates are rigidly connected to the vibration suppressing member on a radial line of the vibration suppressing member.

DETAILED DESCRIPTION OF THE EMBODIMENTS

Embodiments of the present invention will be described hereinafter with reference to FIGS. 1 through 12.

As shown in FIGS. 1 through 5 and 11, a liquid detecting apparatus comprises a liquid detecting element 3 disposed at a lower end of a vibration shaft 1 and immersed in a measuring liquid 2, and a vibrating element 4 disposed at an upper end thereof and conducting a bending vibration in a direction of an axis (vibrating axis) X of the vibration shaft 1.

The vibration shaft 1 is composed of a metal linear rod such as, for example, a stainless steel linear rod, or a synthetic resin or ceramic linear rod.

Figure 4:
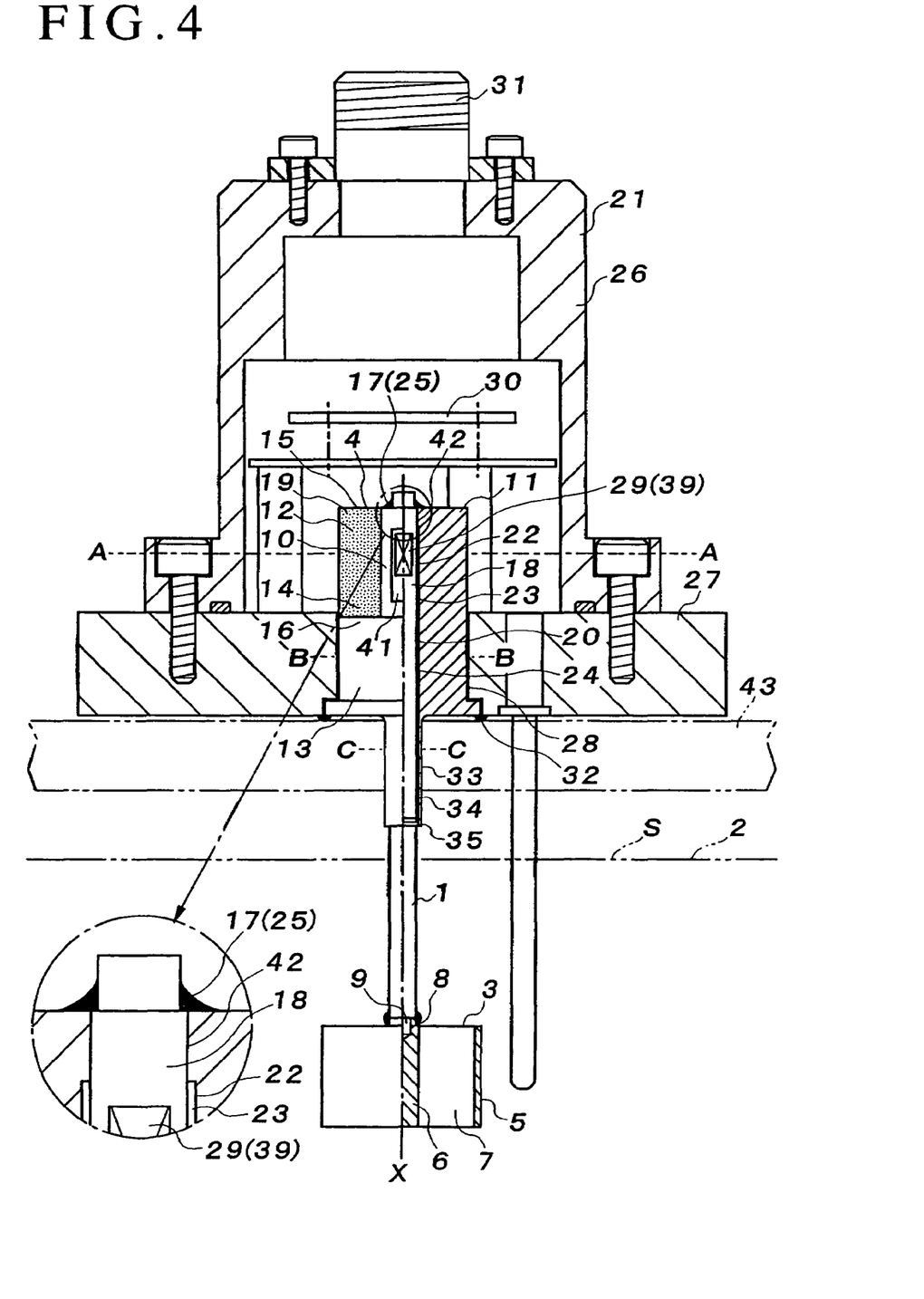
FIG. 4 is a half-vertical sectional view of the liquid detecting apparatus.
Figure 7:
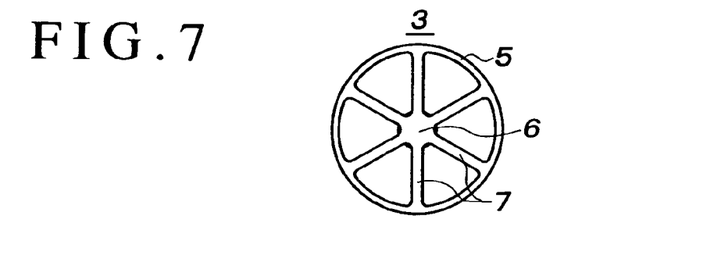
FIG. 7 is a bottom view of a liquid detecting element in the liquid detecting apparatus.

As shown in FIGS. 4 and 7, as well as elsewhere, the liquid detecting element 3 is formed mostly for a density meter. As apparent from those Figures, a plurality of partition walls 7, which extend in a radial direction, are equally spacedly arranged in a peripheral direction between a vertically extending cylindrical part 5 and a shaft part 6 so that the contact area of the liquid detecting element 3 is increased with respect to the measuring liquid 2. The liquid detecting element 3 has a mortise 8 which is open at an upper end face of the shaft part 6. A tenon pin 9 projecting from a lower end face of the vibration shaft 1 is inserted in the mortise hole 8, the upper end face of the shaft part 6 is abutted with the lower end face of the shaft part 1 and welded at the abutting part, so that the liquid detecting element 3 is integrally directly connected to the vibration shaft 1 on the vibration axis X.

Figure 11:
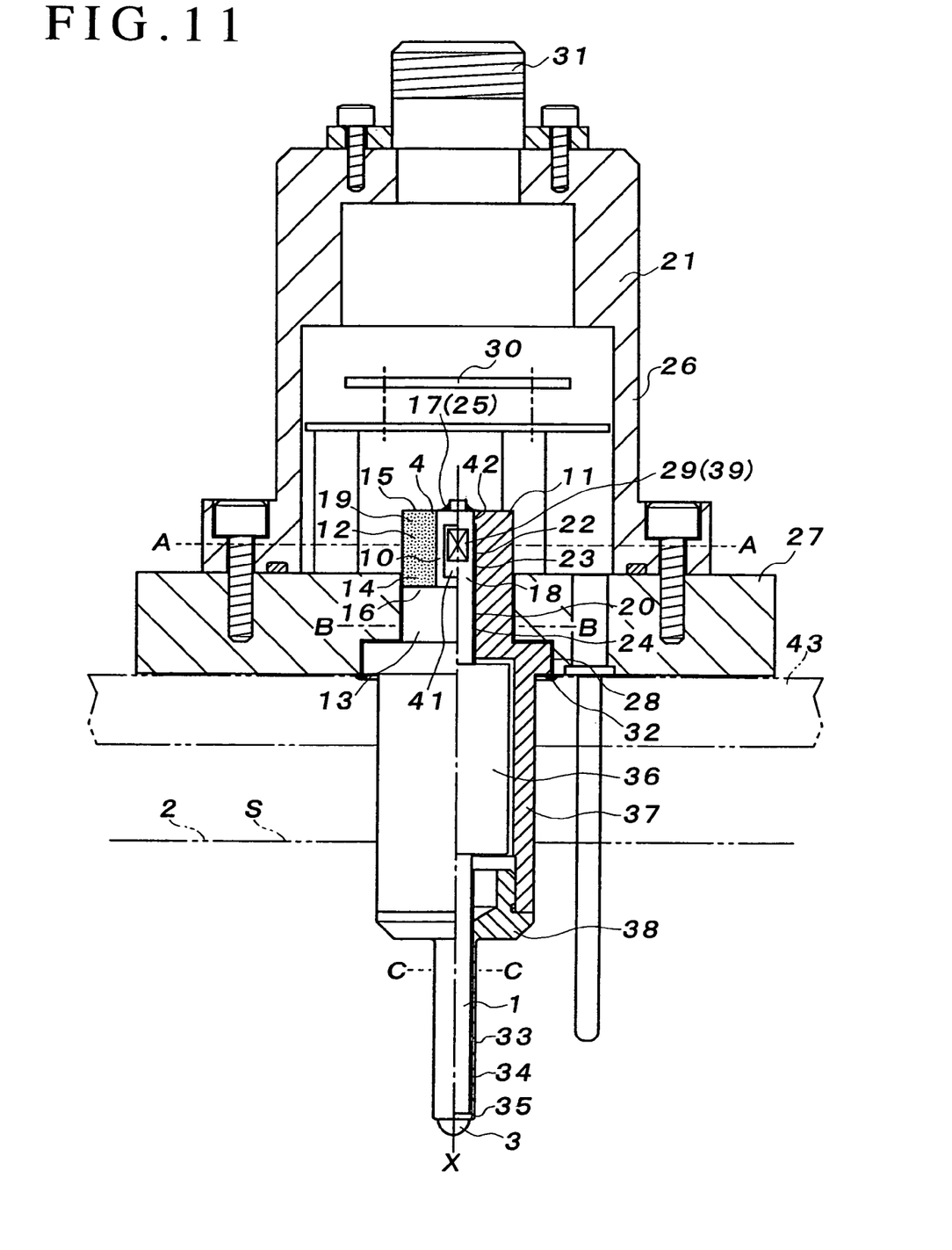
FIG. 11 is a half-cut sectional view showing another example of a specific example of the liquid detecting apparatus.

On the other hand, a liquid detecting element 3 shown in FIG. 11 is formed for a viscometer. This liquid detecting element 3 includes the linear rod-like vibration shaft 1 a lower end part of which is same or enlarged in diameter. Thus, the liquid detecting element 3 forms a part of the vibration shaft 1. It is also an interesting alternative that the liquid detecting element 3 is composed of a circular columnar body or polygonal prism body which is separately formed from the vibration shaft 1, and the liquid detecting element 1 is directly connected to the lower end of the vibration shaft 1 on the vibration axis X in the same manner as mentioned above or by other suitable means.

The liquid detecting element 3 is formed of metal such as stainless steel, or synthetic resin, ceramic or a composite material thereof.

A piezoelectric vibrating plate 19 capable of conducting a bending vibration is used as the vibrating element 4. A plurality of such piezoelectric vibrating plates 19 are axially symmetrically arranged in the axial direction with respect to the vibration shaft so that the piezoelectric vibrating plates 19 conduct a bending vibration. For example, as illustrated, a number, two, of the piezoelectric vibrating plates 19 are spaced apart on a diameter line of the vibration shaft 1.

Figure 1:
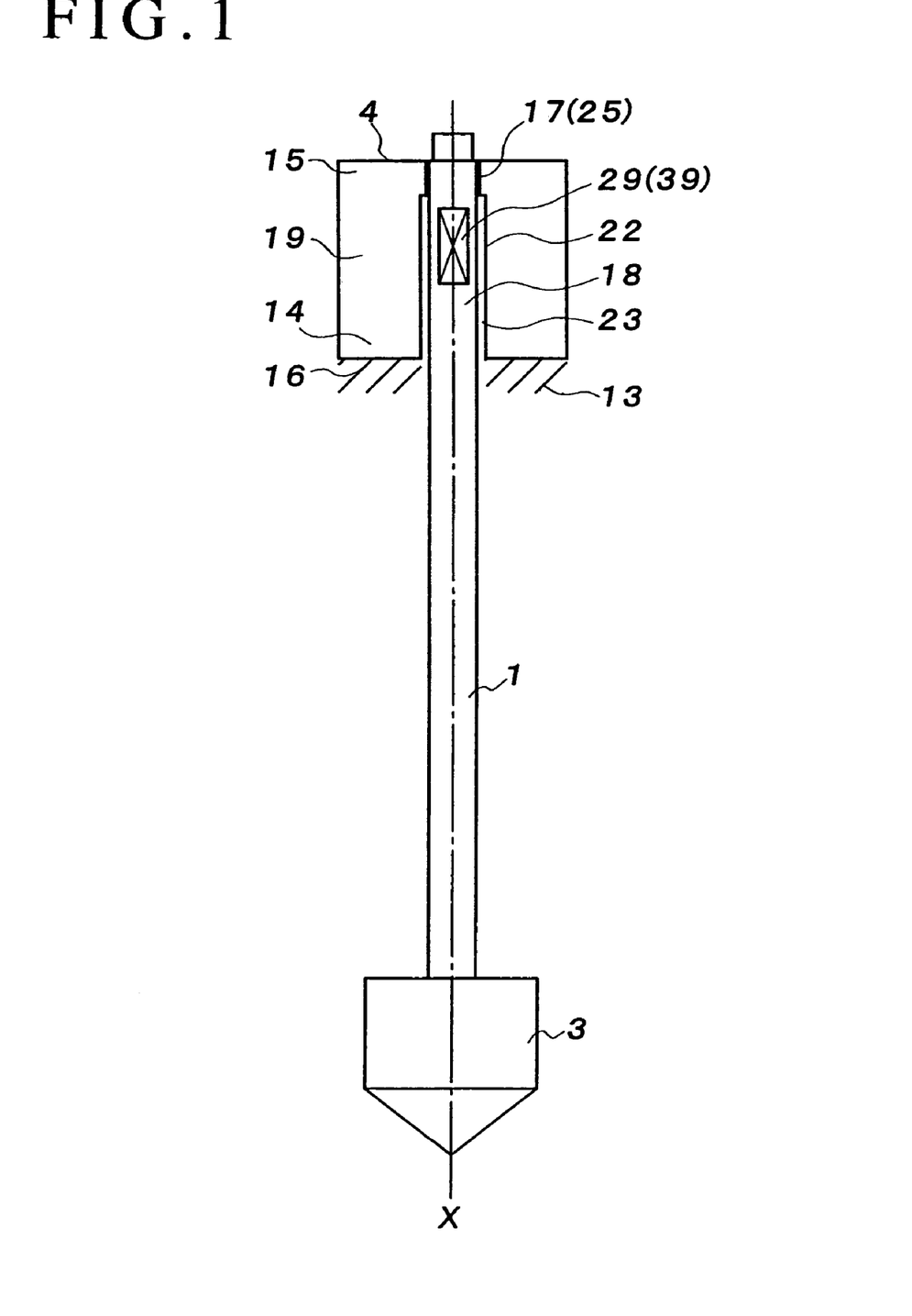
FIG. 1 is a side view showing the basic idea of a vibration structure composed of a vibrating element in a liquid detecting apparatus.
Figure 2:
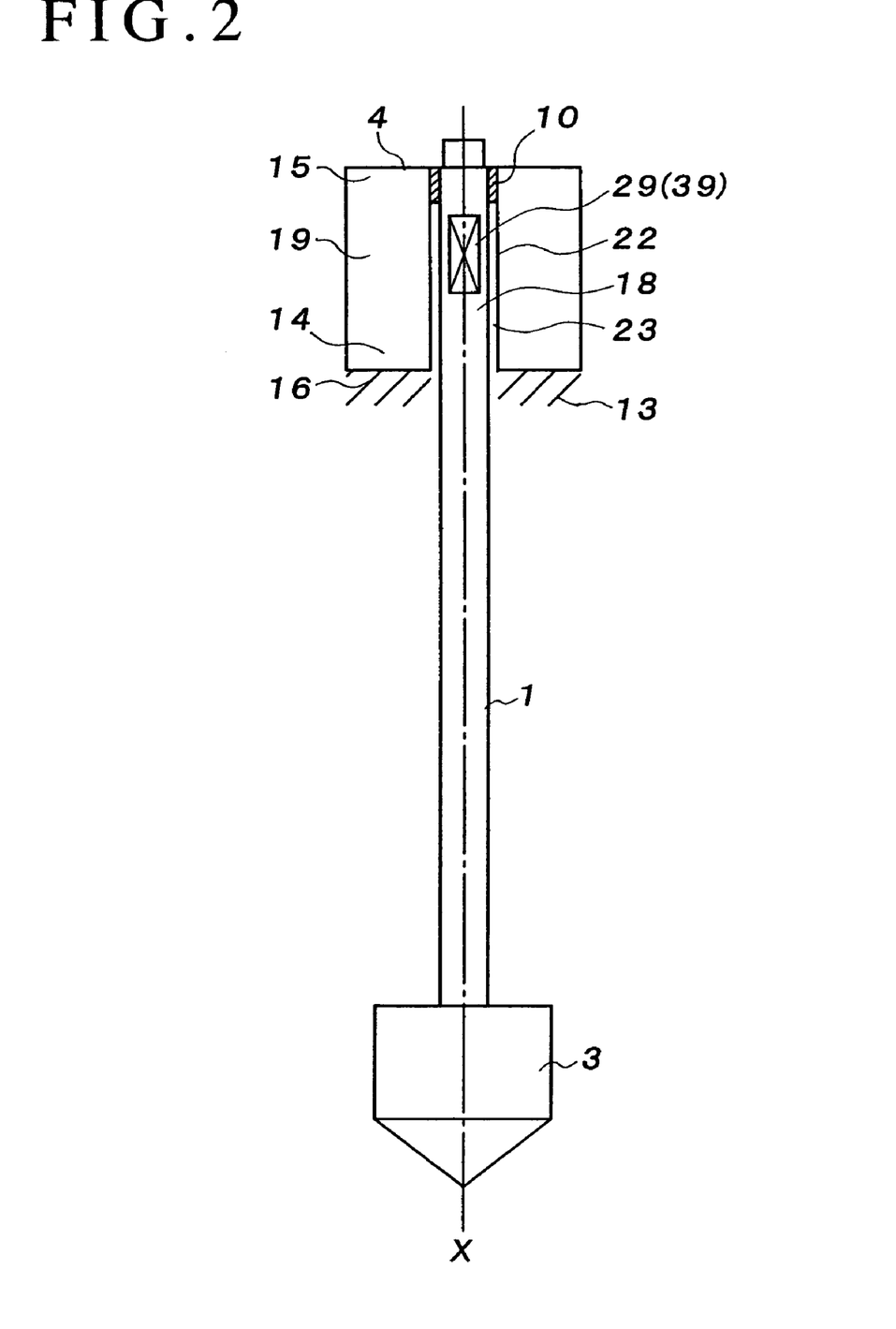
FIG. 2 is a side view showing one example in which the vibrating element is connected to a vibration shaft through a circular cylindrical member in the basic idea of a vibration structure composed of a vibrating element in a liquid detecting apparatus.

As shown in FIGS. 1 and 2, lower vibrating ends on the liquid detecting element 3 side of the piezoelectric vibrating plates 19 are rigidly connected (vibration suppressing connection) to a vibration suppressing member 13 and inner ends of upper vibration ends 15 on the side opposite the liquid detecting element 3 of the piezoelectric vibrating plates 19 are rigidly connected (vibration connection) to the vibration shaft 1.

An inner end edge of each of the piezoelectric vibrating plates 19 excluding the vibration connection part 17 is held free with respect to the vibration shaft 1, a bending vibration at the lower vibrating end of each of the piezoelectric vibrating plates 19 is suppressed on the vibration suppression connection part 17 side and a bending vibration at the upper vibrating end is amplified, the amplified bending vibration at each vibrating end is applied to the vibration shaft 1 and the liquid detecting element 3 through the vibration connection part 17, so that the liquid detecting element 3 is vibrated in the circular direction in the measuring liquid 2.

Figure 3:
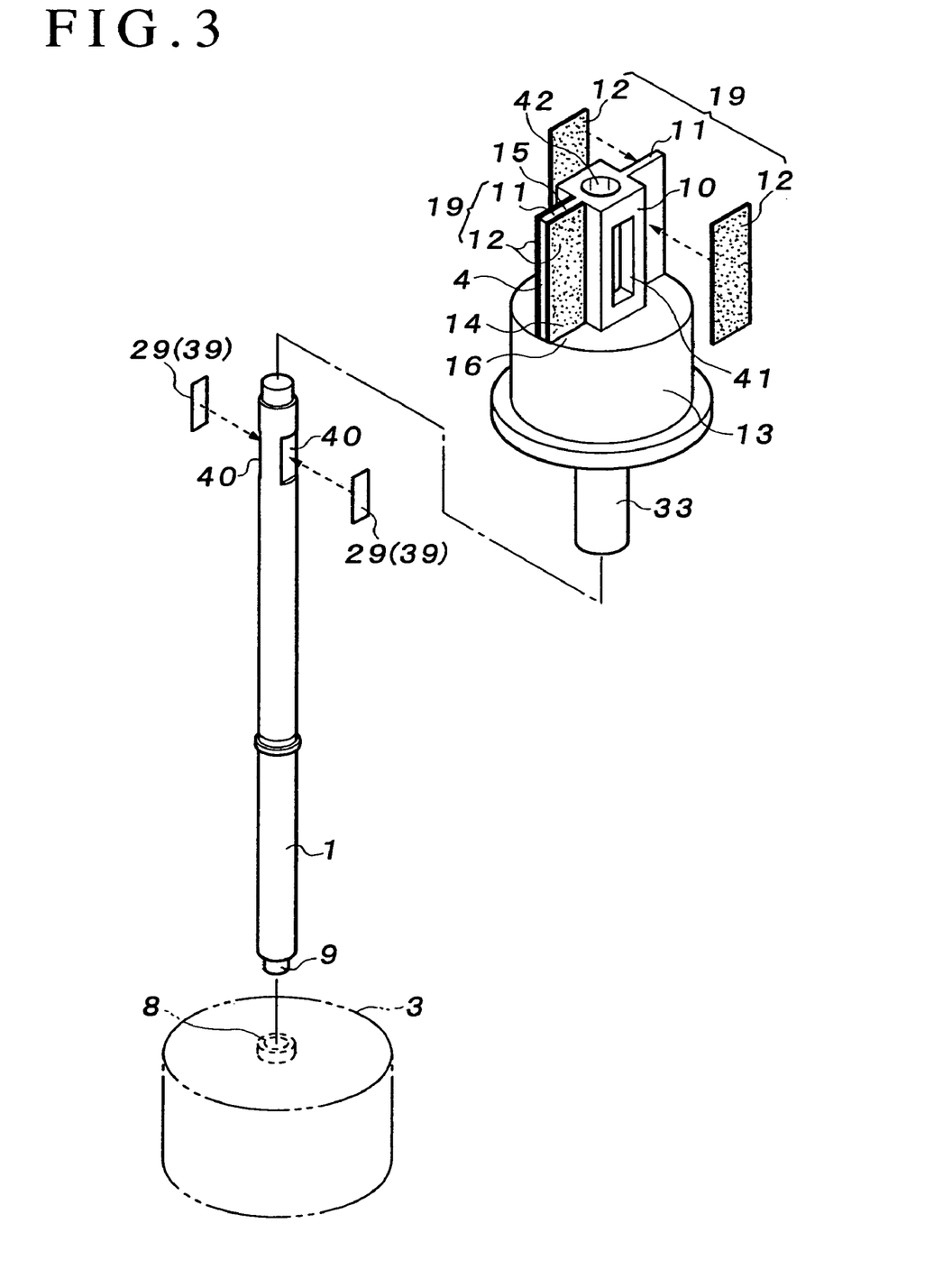
FIG. 3 is an exploded perspective view showing a specific structure of the liquid detecting apparatus.

As a specific example, as shown in FIG. 2 or 3, or in Figures thereafter, a cylindrical member 10 for connecting the inner end edges of the respective piezoelectric vibrating plates 19 (FIG. 3 and subsequent Figures) are connected together or the upper ends of the inner end edges of the respective piezoelectric vibrating plates 19 are connected together, is disposed on the vibrating axis X, each of the piezoelectric vibrating plates 19 is externally inserted in an upper end of the vibration shaft 1 at the cylindrical member 10, lower vibrating ends 14 on the liquid detecting element 3 side of the piezoelectric vibrating plates 19 are rigidly connected (vibration suppressing connection) to a vibration suppressing member 13 and inner ends of upper vibration ends 15 on the side opposite the liquid detecting element 3 of the piezoelectric vibrating plates 19 are rigidly connected (vibration connection) to the vibration shaft 1.

Thus, an inner end edge of each of the piezoelectric vibrating plates 19 excluding the vibration connection part 17 is held free with respect to the vibration shaft 1, a bending vibration at the lower vibrating end 14 of each of the piezoelectric vibrating plates 19 is suppressed on the vibration suppression connection part 16 side and a bending vibration at the upper vibrating end 15 is amplified, the amplified bending vibration at each vibrating end 15 is applied to the vibration shaft 1 and the liquid detecting element 3 through the vibration connection part 17, so that the liquid detecting element 3 is vibrated in the circular direction in the measuring liquid 2.

Figure 12A:
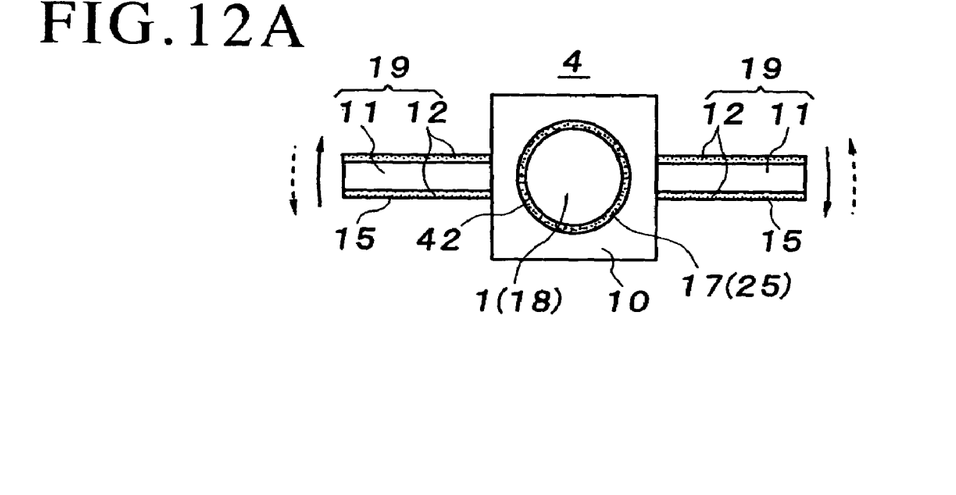
FIG. 12(A) is a plan view for explaining the operation of an upper vibrating end of a vibrating element.
Figure 12B:
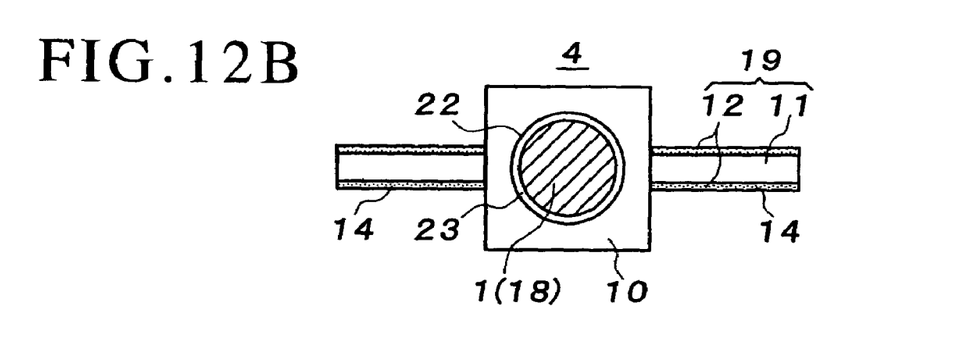
FIG. 12(B) is a bottom view for explaining the operation of a lower vibrating end thereof.
Figure 12C:
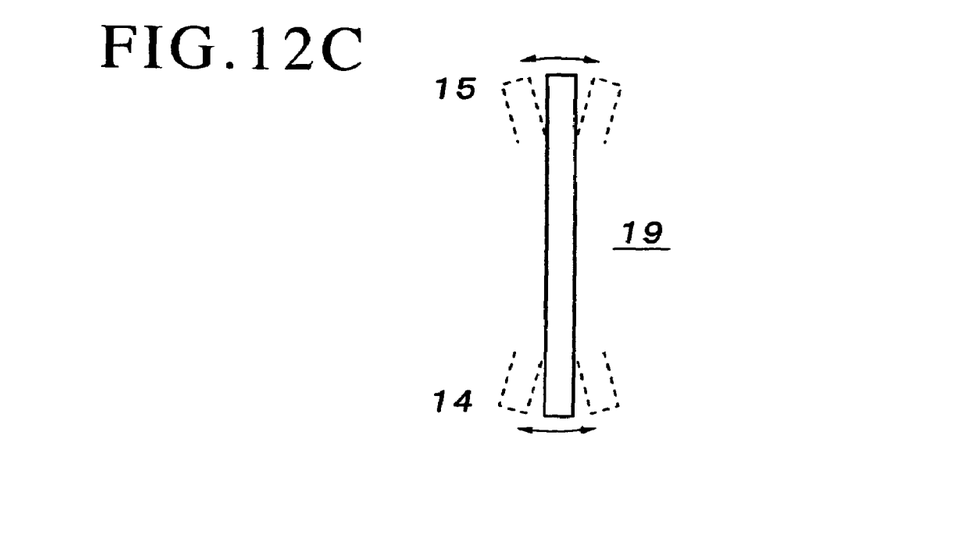
FIG. 12(C) is a side view for explaining the bending vibration of a piezoelectric vibrating plate which forms the vibrating element.

The piezoelectric vibrating plate 19 will be described. This piezoelectric vibrating plate 19 includes a pair of vibrating base plates 11 symmetrically spaced apart leftward and rightward along a diameter line from a generating line of an outer peripheral surface of the cylindrical member 10. As shown in FIGS. 12A–12C, a piezoelectric plate 12 is adhered to one or both surfaces of each vibrating base plate 11, thereby forming a pair of piezoelectric vibrating plates 19 of a bimorph structure. A number, three or more, of such piezoelectric vibrating plates 19 may be arranged at equal spaces in the peripheral direction.

A circular columnar block type vibration suppressing member 13 which serves the vibration axis X as an axis thereof, is integrally disposed at a lower end edge of the piezoelectric vibrating plate 19, i.e., lower end edges of the both vibrating base plates 11, which form the vibrating element 4. Both vibrating base plates 11 are rigidly connected to the suppressing member 13 on the diameter line at the upper end face of the vibration suppressing member 13.

In other words, the vibrating base plate 11 of one of the piezoelectric vibrating plates 19 is rigidly connected at the lower end edge thereof to the vibration suppressing member 13 on the diameter line thereof. Similarly, the vibrating base plate 11 of the other piezoelectric vibrating plate 19 is rigidly connected at the lower end edge thereof to the other radius line on the above-mentioned diameter line to the vibration suppressing member 13.

For example, the cylindrical member 10, the vibrating base plate 11 and the vibration suppressing member 13, which form the vibrating element 4 are integrally formed by cutting. It is also an interesting alternative that the inner end edge, which is parallel to the vibration axis X, of the vibrating base plate 11 is integrally press-fitted or welded to a groove which is formed on a generating line at the outer peripheral surface of the cylindrical member 10.

Similarly, the lower end edge of the piezoelectric vibrating plate 19, i.e., lower end edge of the vibrating base plate 11 is integrally press-fitted or welded to a groove which is formed on a diameter line at the upper surface of the vibration suppressing member 13.

The cylindrical member 10 is composed of a prismatic body or circular columnar body, while the cylindrical member 10, the vibrating base plate 11 and the vibration suppressing member 13 are composed of metal such as stainless steel, or synthetic resin, ceramic or the like.

The upper end of the vibration shaft 1 is inserted in the through-hole 22 which is formed in the cylindrical member 10 of the vibrating element 4, and the vibration suppressing member 13 is rigidly connected (vibration suppressing connection) to the lower vibrating end 14 on the liquid detecting element 3 side in the manner as mentioned above.

The cylindrical member 10 is provided at an upper end of the through-hole 22 with a small bore part 42. This small bore part 42 and a vibration shaft part inserted therein are designed to be approximately the same in diameter. The vibration shaft part is restricted with an inner peripheral surface of the small bore part 42 so as to center the vibration shaft part.

At the same time, the upper vibration end 15 on the side opposite the liquid detecting element 3 of the vibrating element 3 is rigidly connected (vibration connection) at the cylindrical member 10 to the vibration shaft 1 by means of, for example, welding 25, and the shaft part 18 (upper end part of the vibration shaft) extending between the vibration suppressing connection part of the vibration shaft 1 and the vibration connection part 17 is held free with respect to the vibrating element 4.

In other words, as shown in FIG. 1, lower vibrating ends 14 on the liquid detecting element 3 side of the piezoelectric vibrating plates 19 are rigidly connected (vibration suppressing connection) to a vibration suppressing member 13 and inner ends of upper vibration ends 15 on the side opposite the liquid detecting element 3 of the piezoelectric vibrating plates 19 are rigidly connected (vibration connection) to the vibration shaft 1 through or not through the cylindrical member 10, and an inner end edge of each of the piezoelectric vibrating plates 19 excluding the vibration connection part 17 is held free with respect to the vibration shaft 1.

Figure 8:
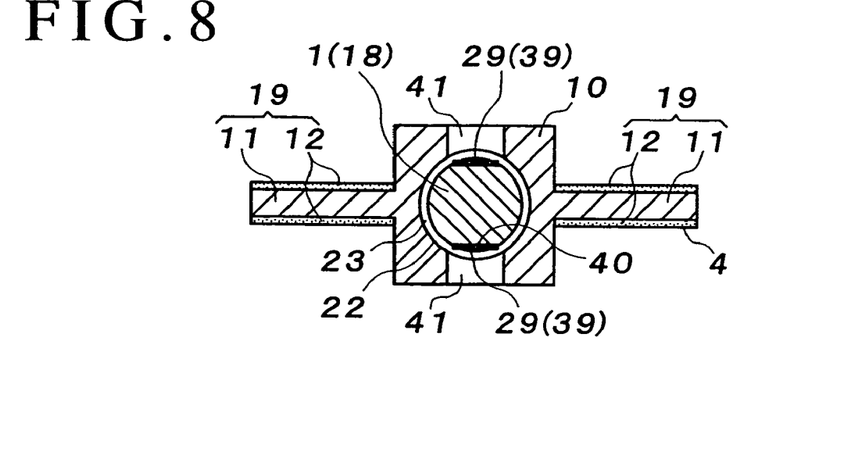
FIG. 8 is a sectional view taken on line A—A of FIGS. 4 and 11.

Thus, as shown in FIG. 8, in case the cylindrical member 10 is elongated along the inner end edge of the piezoelectric vibrating plate 19, a small annular space 23 is formed between the inner peripheral surface of the through-hole 22 of the cylindrical member 10 and the outer peripheral surface of the shaft part 18 which is inserted in the through-hole 22, so that the inner peripheral surface and the outer peripheral surface are held in non-contact relation.

Figure 9:
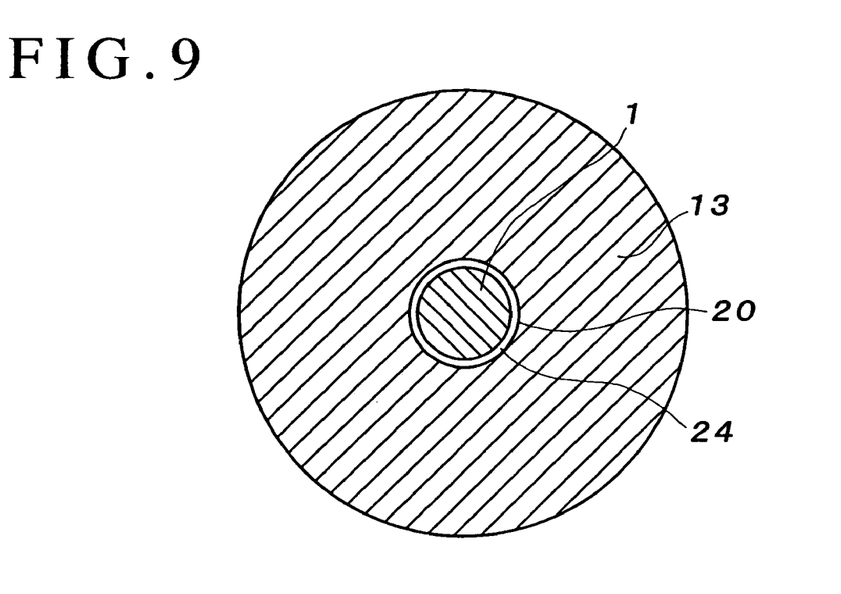
FIG. 9 is a sectional view taken on line B—B of FIGS. 4 and 11.

Similarly, the vibration suppressing member 13 is provided with a through-hole 20 which has the vibration axis X serving as an axis thereof, i.e., a through-hole 20 coaxially communicated with the through-hole 22 of the cylindrical member 10. The upper end part of the vibration shaft 1 is inserted in the through-hole 20. As shown in FIG. 9, a small annular space 24 is formed between the inner peripheral surface of the through-hole 20 and the outer peripheral surface of the shaft part 18, so that the inner peripheral surface and the outer peripheral surface are held in non-contact relation. The vibration suppressing member 13 is a circular columnar body or prismatic body which has the vibration axis X service as the axis thereof.

Referring back again to this arrangement, the upper end part of the vibration axis 1 is inserted in the through-hole 20 of the vibration suppressing member 13 and the cylindrical member 10. The vibrating element 4 and the vibration suppressing member 13 are placed in non-interfering relation through the annular spaces 23, 24. A local part at the tail of the upper end of the vibration shaft 1 is annularly welded to the upper end of the cylindrical member 10.

As shown in FIGS. 4 and 11, the vibration suppressing member 13 is rigidly connected to an envelope 21 which receives therein the vibration suppressing member 13 and the vibrating element 4.

The envelope 21 comprises an envelope main body 26 and an installed flange 27 mounted on a lower end of the envelope main body 26. The installed flange 27 is provided at a central part thereof with a through-hole 28 which has the vibration axis X serving as an axis thereof. While receiving the vibration suppressing member 13 in the through-hole 28, the vibrating element 4 and the shaft part 18 inserted therein are received in the envelope main body 26.

A lower peripheral edge part of the vibration suppressing member 13 is annularly welded at a lower end peripheral edge part of the through-hole 28 of the installed flange 27 so as to be integrally rigidly connected thereto. The vibration shaft 1 further extends downward from the through-hole 28 of the installed flange 27 and has the liquid detecting element 3 formed at a lower end thereof.

The liquid detecting apparatus is attached to a measuring liquid envelope 43 such as piping for passing the measuring liquid 2 or a tank containing the measuring liquid 2 through a bolt or the like. Accordingly, the vibration suppressing member 13 is substantially rigidly connected to the envelope 43 of the measuring liquid 2 through the envelope 21. In this case, the vibration suppressing member 13 functions as a vibration stopping means which further enhances the vibration suppressing function.

By fixedly attaching the liquid detecting apparatus to the measuring liquid envelope 43 through the installed flange 27, at least the liquid detecting element 3 is immersed in the measuring liquid 2 within the envelope 43. Reference character S denotes a liquid surface of the measuring liquid 2.

Figure 5:
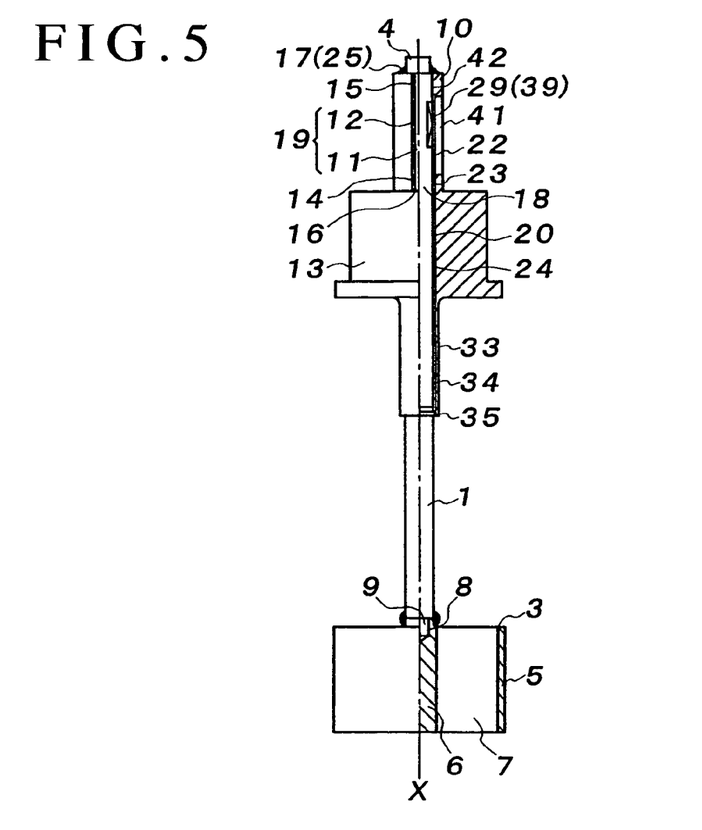
FIG. 5 is a half-vertical sectional view of a vibration unit in the liquid detecting apparatus when viewed after it is rotated at 90 degrees.
Figure 6:
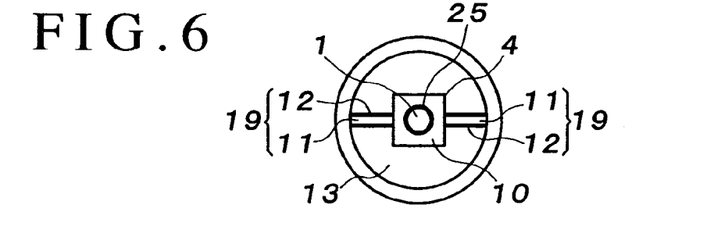
FIG. 6 is a plan view of the liquid detecting apparatus.
Figure 10:
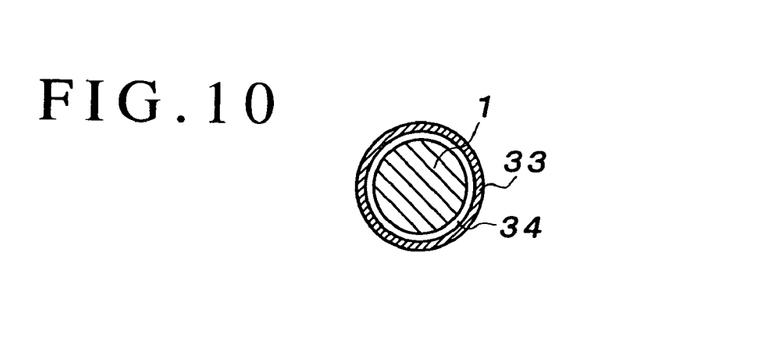
FIG. 10 is a sectional view taken on line C—C of FIGS. 4 and 11.

In the liquid detecting apparatus shown in FIGS. 3 through 5, a spring cylinder 33, which has the vibration axis X serving as an axis thereof, is allowed to suspend from a central part of the lower end of the vibration suppressing member 13. As shown in FIG. 10, the vibration shaft 1 is inserted in the spring cylinder 33 with a small annular space 34 left therebetween. A lower end of the spring cylinder 33 is fixed at fixed part 35 to an intermediate part of the vibration shaft 1 extending from the vibration suppressing member 13.

Accordingly, the vibration shaft 1 is supported at two points by the vibration connection part 17 and the fixed part 35 and allowed to further extend from the spring cylinder 33 to have the liquid detecting element 3 attached to the lower end thereof. In other words, the integral unit of the vibration suppressing member 13 and the piezoelectric vibrating plate 19 is supported at two points of the vibration connection part 17 and the fixed part 35 through the spring cylinder 33 with respect to the vibration shaft 1 such that the centers of the vibration suppressing member 13 and the piezoelectric vibrating plate 19 are held on the axis.

On the other hand, in the liquid detecting apparatus shown in FIG. 11, a massive body 36 for adjusting the resonance frequency is coaxially attached to an intermediate part of the vibration shaft 1 which extends from the envelope 21. The massive body 36 is covered with a seal case 37.

The seal case 37 is made of metal, synthetic resin, ceramics, or the like. As illustrated, the seal case 37 is integrally connected such that its upper end is coaxial with the lower end of the vibration suppressing member 13 and allowed to suspend from the lower end of the vibration suppressing member 13 to cover the massive body 36.

For example, the vibrating base plate 11, the vibration suppressing member 13 and the cylindrical part of the seal case 37 are formed of a unitary part obtained by cutting. In case the spring cylinder 33 is provided, those four components 11, 13, 37 and 33 are formed of a unitary part obtained by integral cutting.

The seal case 37 has a bottom plate 38 for closing its lower end face. The spring cylinder 33, which has the vibration axis X serving as an axis thereof, is allowed to suspend from the central part of the lower end face of the bottom plate 38. As shown in FIG. 10, the vibration shaft 1 is inserted in the spring cylinder 33 with a small annular space 34 left therebetween, and the lower end of the spring cylinder 33 is fixed at the fixed part 35 to an area in the vicinity of the lower end of the vibration shaft 1 extending from the vibration suppressing member 13.

Each spring cylinder 33 is very small in thickness and has resilience to enable it to make a circular direction vibration following the circular direction vibration of the vibration shaft 1 while supporting the vibration shaft 1.

Within the envelope main body 26, there are disposed a driver circuit for feeding a driving voltage to the vibrating element 4 and a circuit board 30 for forming, among others, a circuit for amplifying the output of a vibration sensor 29 as later described. The circuit board 30 and an external power source or control circuit are wire-connected through a connector 31 which is disposed at a wall which defines the envelope main body 26. It is also accepted that without providing this connector 31, the above-mentioned wire-connecting can be achieved through a wiring port formed in the wall which defines the envelope main body 26 from the circuit board 30.

The piezoelectric vibrating plate 19, which forms the vibrating element 4, originally includes, as shown in FIG. 12(C), an upper vibrating end 15 on the upper end side of the vibration axis X, and a lower vibrating end 14 on the lower end side. The upper vibration end 15 and the lower vibration end 14 conduct a bending vibration in the direction of the thickness, alternately and cyclically.

Since the lower vibrating end 14 of each piezoelectric vibrating plate 19 is rigidly connected to the vibration suppressing member 13 in the manner as mentioned above, as shown in FIG. 12(B), vibration of the lower vibrating end 14 is stopped. As indicated by arrows in FIG. 12(A), the upper vibrating end 15 of one piezoelectric vibrating plate 19 and the upper vibrating end 15 of the other piezoelectric vibrating end 19 mutually conduct a bending vibration clockwise or counterclockwise.

Thus, the bending vibration of the upper vibrating end of the upper vibrating element 4 is amplified on the vibration connection part 17 side, and the amplified bending vibration of the upper vibrating end 15 is transmitted to the vibration shaft 1 and the liquid detecting element 3 through the vibration connection part 17 disposed at the inner end of the upper vibrating end 15, so that the liquid detecting element 3 is soundly vibrated in the circular direction in the measuring liquid 2.

Variation in vibration of the liquid detecting element 3 in the measuring liquid 2 is detected by the vibration sensor 29 and outputted to an external apparatus through the circuit board 30.

The vibrating element 4, i.e., piezoelectric vibrating plate 19 is an electromechanical converting element which is shifted in accordance with an electric signal, while the vibration sensor 29 is a mechano-electrical converting element which outputs an electric signal by vibration. This vibration sensor 29 is formed by adhering a piezoelectric plate 39 or torsion element to an upper end of the vibration shaft 1, preferably in a region where the piezoelectric vibrating plate 19 extends, i.e., the upper end shaft part 18 of the vibration shaft 1 within the cylindrical member 10 in this embodiment.

In case the vibration shaft 1 is formed of a circular rod, as illustrated, planar adhesion surfaces 40 are disposed at the opposing side surfaces of the vibrating shaft 1, and the piezoelectric plate 39 or torsion element is adhered to each adhesion surface 40.

Through windows 41 opposing the adhesion surfaces 40 are disposed at the opposing side walls of the cylindrical member 10, and the piezoelectric element 30 or torsion element is adhered through this through window 41. It is also an interesting alternative that the adhered piezoelectric plate 39 or torsion element is preliminarily placed opposite the window 41 so that inspection for correction can be made available. The through window 41 also functions as a heat releasing window to allow for the release of heat from the piezoelectric plate 39 or torsion element.

According to the present invention, the bending vibration of the upper vibrating end of the upper vibrating element is amplified, and the amplified bending vibration is transmitted to the vibration shaft and the liquid detecting element through the vibration connection part, so that the liquid detecting element can be soundly vibrated in the circular direction in the measuring liquid.

Although the present invention has been described in its preferred form with a certain degree of particularity, it should be understood that the present disclosure of the preferred form has been made only by way of example and that numerous changes in the details of construction and arrangement of parts may be resorted to without departing from the spirit and the scope of the invention as hereinafter claimed.

What is claimed is:

1. A liquid detecting apparatus comprising a liquid detecting element disposed at a lower end of a vibration shaft to be immersed in a measuring liquid, and a vibrating element disposed at an upper end of said vibration shaft and for vibrating said vibration shaft in a circular direction about an axis thereof, wherein a plurality of piezoelectric vibrating plates, which each conduct a bending vibration, are used as said vibrating element and axially symmetrically arranged in the axial direction with respect to said vibration shaft so that said piezoelectric vibrating plates conduct a bending vibration, lower vibrating ends on the liquid detecting element side of said piezoelectric vibrating plates are rigidly connected to a vibration suppressing member and inner ends of upper vibration ends on the side opposite said liquid detecting element of said piezoelectric vibrating plates are rigidly connected to said vibration shaft, an inner end edge of each of said piezoelectric vibrating plates excluding the vibration connection part is held free with respect to said vibration shaft, a bending vibration at the lower vibrating end of each of said piezoelectric vibrating plates is suppressed on the vibration suppression connection part side and a bending vibration at the upper vibrating end is amplified, the amplified bending vibration at each vibrating end is applied to said vibration shaft and said liquid detecting element through the vibration connection part, so as to vibrate said liquid detecting element in the circular direction in said measuring liquid, wherein a through-hole having the vibration axis serving as an axis thereof is formed in said vibration suppressing member, said vibration shaft is inserted in said through-hole and said piezoelectric vibrating plates are rigidly connected to said vibration suppressing member on a radial line of said vibration suppressing member.

2. A liquid detecting apparatus comprising a liquid detecting element disposed at a lower end of a vibration shaft to be immersed in a measuring liquid, and a vibrating element disposed at an upper end of said vibration shaft and for vibrating said vibration shaft in a circular direction about an axis thereof, wherein a plurality of piezoelectric vibrating plates, which each conduct a bending vibration, are used as said vibrating element and axially symmetrically arranged in the axial direction with respect to said vibration shaft so that said piezoelectric vibrating plates conduct a bending vibration, a cylindrical member is provided and has as an axis thereof the vibration axis for connecting the inner end edges of said piezoelectric vibrating plates, each of said piezoelectric vibrating plates is externally inserted in an upper end of said vibration shaft at said cylindrical member, lower vibrating ends on the liquid detecting element side of said piezoelectric vibrating plates are rigidly connected to a vibration suppressing member and inner ends of upper vibration ends on the side opposite said liquid detecting element of said piezoelectric vibrating plates are rigidly connected to said vibration shaft, an inner end edge of each of said piezoelectric vibrating plates excluding the vibration connection part is held free with respect to said vibration shaft, a bending vibration at the lower vibrating end of each of said piezoelectric vibrating plates is suppressed on the vibration suppression connection part side and a bending vibration at the upper vibrating end is amplified, the amplified bending vibration at each vibrating end is applied to said vibration shaft and said liquid detecting element through the vibration connection part, so as to vibrate said liquid detecting element in the circular direction in said measuring liquid, wherein a through-hole having the vibration axis serving as an axis thereof is formed in said vibration suppressing member, said vibration shaft is inserted in said through-hole and said piezoelectric vibrating plates are rigidly connected to said vibration suppressing member on a radial line of said vibration suppressing member.

* * * * *